United States Patent [19]

Fernandez et al.

[11] Patent Number: 5,449,845
[45] Date of Patent: Sep. 12, 1995

[54] PURIFICATION OF SATURATED HALOCARBONS

[75] Inventors: Richard E. Fernandez, Bear; Wendel R. Cassel, Newark, both of Del.

[73] Assignee: E. I. Du Pont de Nemours and Company, Wilmington, Del.

[21] Appl. No.: 591,221

[22] Filed: Oct. 2, 1990

Related U.S. Application Data

[63] Continuation of Ser. No. 487,436, Mar. 2, 1990, abandoned, which is a continuation of Ser. No. 275,063, Nov. 22, 1988, abandoned.

[51] Int. Cl.$^6$ ............................................. C07C 17/38
[52] U.S. Cl. ..................................................... 570/177
[58] Field of Search ................................. 570/179, 177

[56] References Cited

U.S. PATENT DOCUMENTS 2,999,885  9/1961  Heberling .

FOREIGN PATENT DOCUMENTS 1362909  8/1974  United Kingdom .

OTHER PUBLICATIONS

Musick and Williams, Ind. Eng. Chem., Prod. Res. Develop. vol. 13, No. 3, 1974, pp. 175–179.

*Primary Examiner*—Alan Seigel
*Attorney, Agent, or Firm*—James E. Shipley

[57] ABSTRACT

A process for reducing the content of unsaturated impurities in saturated fluorohalocarbons and fluorohalohydrocarbons by contacting the impure saturated fluorohalocarbon and/or fluorohalohydrocarbon in a substantially dry fluid state with a substantially dry amorphous solid metal oxide composition consisting essentially of cupric oxide, cobaltic oxide, silver oxide, manganese dioxide, or a mixture of any two or more thereof, at an effective temperature up to about 300° C.

15 Claims, No Drawings

PURIFICATION OF SATURATED HALOCARBONS

CROSS-REFERENCE TO RELATED APPLICATIONS

This application is a continuation of and priority is claimed to U.S. patent application Ser. No. 07/487,436, filed Mar. 2, 1990, now abandoned, which is a continuation of U.S. patent application Ser. No. 07/275,063, filed Nov. 22, 1988, now abandoned.

BACKGROUND OF THE INVENTION

This invention relates to the purification of saturated fluorohalocarbons and fluorohalohydrocarbons containing unsaturated impurities, and in particular to an oxidative process for removing unsaturated impurities from the hydrogen-containing members of said saturated halocarbons having 2 to 6 atoms.

Saturated fluorohalocarbons such as chlorofluorocarbons having 2 to 6 carbon atoms are, when pure, inert and non-toxic gases and liquids at ordinary temperatures and pressures, and are useful, among other applications, as refrigerants, propellants, blowing agents, solvents and intermediates for the production of other halogenated products.

Hydrogen-containing fluorocarbons and chlorofluorocarbons, are currently of interest as replacements for many of the commercially employed perchlorofluorocarbons because of their greatly reduced ozone depletion potentials.

In the manufacture of the saturated fluorohalocarbons and fluorohalohydrocarbons, undesirable unsaturated by-products are often also formed and contaminate the desired products. The unsaturated compounds are highly objectionable as contaminants as they are often toxic, and for most uses their concentrations in the saturated product must be lowered to innocuous levels of 10 ppm or less. Distillation and other conventional physical methods which may be used for their removal to acceptable levels are, however, generally ineffective or too costly. Accordingly, various chemical treatments have been heretofore proposed for this purpose; for example:

Heberling, U.S. Pat. No. 2,999,855 (1961) discloses that unsaturated fluorocarbons and saturated fluorohydrocarbons can be removed from saturated perfluorocarbon product streams by treatment with aqueous alkaline potassium permanganate at 20° to 95° C.

Weeks, U.S. Pat. No. 3,696,156 (1972) proposes to remove unsaturates from saturated perfluorohalocarbons by contacting the impure material in the vapor phase at 180° to 250° C. with alumina containing an alkali metal or alkaline earth metal hydroxide.

Bell, U.S. Pat. No. 4,129,603 (1978) discloses that the content of by-product 1,1-di fluoro-2-chloroethylene, $CF_2=CHCl$, in 1,1,1,2-tetrafluoroethane, $CF_3CH_2F$, produced by vapor phase hydrofluorination of a 1,1,1-trihalo-2-chloroethane over a chromium oxide catalyst at 300°–400° C., can be reduced by contacting the impure product with aqueous alkaline metal permanganate at 10° to 40° C. There is no disclosure as to possible loss of some of the fluorohydrocarbon, $CF_3CH_2F$, during the alkaline permanganate treatment in view of the above Heberling disclosure.

On the other hand, Potter, U.S. Pat. No. 4,158,675 (1979) teaches the removal of 1,1-difluoro-2-chloroethylene from the 1,1,1,2-tetrafluoroethane product stream produced as in Bell above by vapor phase hydrofluorination of a 1,1,1-trihalo-2-chloroethane, by passing the impure stream together with hydrogen fluoride over a chromium oxide catalyst at lower temperatures (100°–275° C.) than the hydrofluorination temperatures (300°–400° C.) of the tetrafluoroethane production step.

None of these prior processes is entirely satisfactory from a commercial standpoint. The aqueous alkaline metal permanganate treatments of the Heberling and Bell patents, for example, require that the halocarbon products exiting the treatment medium be dried (separated from its entrained water) before further refining, which adds to the expense of the treatment. Moreover, where saturated halohydrocarbon products are being treated, the possibility exists that some of the valuable saturated material could be lost to the alkaline oxidative medium along with the unsaturated impurities.

On the other hand, the high temperatures of the Weeks and Potter treatments are objectionable because the higher temperatures increase the cost of removing the unsaturated impurities. Further, the Weeks treatment appears limited to perhalocarbons inasmuch as hydrogen-bearing halohydrocarbons are possibly susceptible to dehydrohalogenation to form unsaturated products under the high temperature alkaline conditions of the disclosed process.

Frazer and Scalione, U.S. Pat. No. 1,345,323 (1922) describe the preparation and use of certain amorphous metal oxides as catalysts suitable for the oxidation of readily oxidizable gases, for example, carbon monoxide, ammonia, sulfur dioxide, aldehydes, alcohols and toluene, by passing them mixed with oxygen or air through the catalyst at ordinary or only slightly elevated temperatures. Included among the metal oxides are cupric oxide, silver oxide, cobaltic oxide, manganese dioxide and intimate mixtures of the metal oxides called hopcalites, such as, for example, $CuO-MnO_2$, $Ag_2O-MnO_2$, $Co_2O_3-MnO_2$ and $CuO-Ag_2O-Co_2O_3-MnO_2$.

A later publication, Johnson and Gammon, U.S. Naval Research Laboratory Report NRL 6582, dated Jul. 20, 1967, describes a study of the decomposition of methylchloroform, vinylidene chloride, trichloroethylene or tetrachloroethylene when exposed in humid air at temperatures up to 300° C. to a hopcalite catalyst that is a co-precipitate of cupric oxide and manganese dioxide. The percentage decomposition of the chlorocarbons increased with increasing temperature. At 300° C., it ranged from 70% for tetrachloroethylene to 100% for methylchloroform. All the chlorocarbons yielded by-product hydrogen chloride under the decomposition conditions.

Musick and Williams, Ind. Eng. Chem., Prod. Res. Develop, Vol. 13, No. 3, 1974, pages 175–179, describes a broader follow-up study involving 19 halogenated hydrocarbons. The halocarbons, mixed with humid air, were each exposed to a hopcalite catalyst based on cupric oxide and manganese dioxide in a catalytic burner operated at 305° and 315° C. Seven of the compounds, all saturated perhalocarbons having high fluorine contents, showed no detectable loss at 305° or 315° C. Another 9 saturated compounds, including the halohydrocarbons chloroform, dichlorofluoromethane, chlorodifluoromethane, methyl chloroform and 1,1,1-trifluoro-2-chloroethane, suffered significant decomposition losses under the same oxidative conditions. The remaining 3 compounds, all unsaturated, namely vinylidene chloride, trichloroethylene and tetrachloroethylene, were extensively decomposed. Hydrogen halide was again detected in the burner effluents of all the halocarbons undergoing decomposition loss. The presence of hydrogen halide is objectionable since additional processing is needed to remove it.

It is an object of this invention to provide a new and effective oxidative process for reducing the concentration of unsaturated impurities in fluorohalocarbons and fluorohalohydrocarbons, in particular in such halocarbons having 2 to 6 carbon atoms and where halo represents one or more fluoro, chloro and/or bromo groups.

Another object is to provide a process as above that operates at relatively low temperatures.

Still another object is to provide a process as above that reduces the unsaturated impurity content of fluorohydrocarbon and chlorofluorohydrocarbon product streams substantially without yield loss of the hydrogen-bearing halocarbon components.

A further object is to provide a process as above that is effective in lowering the unsaturated impurity content of the saturated product streams to low levels without the coproduction of hydrogen halides, thereby facilitating the direct recovery of the saturated products.

SUMMARY OF THE INVENTION

A process has been discovered for reducing the content of unsaturated impurities in saturated fluorohalocarbons and/or fluorohalohydrocarbons comprising
contacting said impure saturated fluorohalocarbons and/or fluorohalohydrocarbons in a substantially dry, fluid state with a substantially dry, amorphous solid metal oxide composition consisting essentially of cupric oxide, cobaltic oxide, silver oxide, manganese dioxide, or a mixture of any two or more thereof, at an effective temperature and, thereafter,
recovering said saturated fluorohalocarbons and/or fluorohalohydrocarbons having a reduced content of said unsaturated impurities.

Such treatment enables the recovery of the saturated products directly which are substantially free of its unsaturated impurities. It also enables the recovery of said saturated products, not only substantially free of unsaturates, but substantially free of water and by-product hydrogen halides as well. Further, it enables fluorohalohydrocarbons treated in accordance with the method of invention to be recovered substantially completely unsaturate-free without yield loss.

DETAILED DISCLOSURE OF THE INVENTION

In general, the invention process is conducted by contacting, either batchwise or continuously, a substantially dry, impure saturated fluorohalocarbon and/or fluorohalohydrocarbon in gaseous or liquid form with a substantially dry, amorphous solid metal oxide composition, generally in particulate form. It is preferably conducted as a continuous process wherein a gaseous stream of the impure halocarbon is passed through a particulate solid bed of the metal oxide composition disposed, for example, in a pipeline reactor and maintained at the desired temperature by heating, if necessary.

The exit stream from the reactor, with the saturated material substantially depleted of its content of unsaturated impurities and now containing oxidation product carbon dioxide, can be treated, if desired, by conventional means for separating the saturated halocarbon product from the carbon dioxide by-product, for instance, by contacting with a solid adsorbent for $CO_2$ such as soda lime, NaOH deposited on vermiculite or a molecular sieve, e.g., a 4A type molecular sieve. Reaction of $CO_2$ with NaOH forms $Na_2CO_3$ and $H_2O$, with the $H_2O$ bound to the $Na_2CO_3$ as hydrates. Since the hydrates are decomposable at elevated temperatures, it is advisable to pass the halocarbon product exiting the $CO_2$ absorber through a bed of a $H_2O$-adsorbing molecular sieve if minimum moisture content product is desired.

In contrast to the hopcalite catalyst-use art, the invention process does not depend on catalytic oxidation of the unsaturated impurities in the presence of a source of molecular oxygen, such as air or other oxygen-containing gas. In other words, molecular oxygen as reactant is not necessary to the success of the process and, although it can be present, it is preferably absent.

How the metal oxide composition functions to remove unsaturates from the saturated halocarbons is not fully understood. It is believed, however, in part to involve oxidation of the unsaturates to carbon dioxide with oxygen supplied by the metal oxide composition itself, and in part to involve adsorption of the unsaturates on the surface of the metal oxide composition through coordination of the unsaturated bonds of the impurities with cationic species of the solid composition. Whatever the mechanism, the process is highly effective in lowering the content of a wide variety of unsaturated hydrocarbons and halocarbons in saturated fluorohalocarbons and fluorohalohydrocarbons to low levels.

The invention is applicable to the purification of saturated fluorohalocarbons and fluorohalohydrocarbons and mixtures thereof, whatever their source, that contain one or more fluorine atoms in the molecule and are contaminated with unsaturated, usually olefinic, impurities. The saturated fluorine-containing halocarbons and halohydrocarbons are preferably those wherein halo is fluoro, chloro or bromo; in particular, wherein halo is fluoro and/or chloro for reasons of their broader utility and greater commercial importance. Included are perhalo- and halohydrocarbons composed of: carbon and fluorine; carbon, chlorine and/or bromine and fluorine; carbon, hydrogen and fluorine; and carbon, hydrogen, chlorine and/or bromine and fluorine. The saturated fluorohalocarbons and fluorohalohydrocarbons preferably contain 2 to 6 carbon atoms, more preferably 2 to 3, most preferably 2 because of their greater commercial importance, and will have normal boiling points in the range $-80°$ to $130°$ C., more usually $-40°$ to $120°$ C. The fluorohalohydrocarbons where halo stands for one or more fluorine atoms, with chlorine atoms optionally present, constitute a highly preferred embodiment of the invention because of the low ozone-depletion potentials of such compounds.

The saturated fluorohalocarbons and fluorohalohydrocarbons include alicyclic as well as acyclic compounds represented by the empirical formula $C_nH_mF_pX_q$, where X is Cl, and/or Br, preferably Cl, and n is an integer from 2 to 6, m is an integer from 0 to 13, p is an integer from 1 to 14 and q is an integer from 0 to 7, provided that $m+p+q$ equals $2n+2$ when the compound is acyclic and equals $2n$ when the compound is alicyclic.

In one embodiment the fluorinated halocarbons are alkanes, i.e. acyclic, represented by the above empirical formula where n is 2 or 3, m is 0 to 7, p is 1 to 8 and q is 0 to 4 when X is Cl and 0 to 3 when X is Br.

In another embodiment the fluorinated halocarbons are acyclic hydrogen-bearing alkanes, where n is 2, m is 1 to 5, p is 1 to 5, X is Cl, q is 0 to 4 and m+p+q is 6.

In still another embodiment the compounds to be treated are fluorinated hydrogen-bearing alkanes where n is 3, m is 1 to 7, p is 1 to 7, X is Cl, q is 0 to 3 and m+p+q is 8.

In all the above embodiments p, designating the number of fluorines in the molecule, is preferably greater than 1.

Representative saturated halocarbons that can be treated in accordance with the method of the invention when contaminated with unsaturated impurities include fluorohalocarbons such as $CCl_3CCl_2F$, $CCl_2FCCl_2F$, $CCl_3CClF_2$, $CClF_2CCl_2F$, $CF_3CCl_3$, $CClF_2CClF_2$, $CCl_2FCF_3$, $CClF_2CF_3$, $CF_3CF_3$, $CF_3CCl_2Br$, $CF_3CClBr_2$, $CF_3CBr_3$, $CBrF_2CBrF_2$, $CBrF_2CF_3$, $CClF_2CF_2CCl_3$, $CF_3CF_2CF_3$, $CF_3CF_2CF_2CCl_3$, $CF_3CF_2CF_2CF_3$, $CF_3CF_2CF_2CF_2CF_3$, $(CF_3)_2CF_2CF_2CF_3$, $CF_3CFCF_2CF_2CFCF_3$, $CF_3CFCF_2CF(CF_3)CF_2$, $CF_3CF_2CF_2CClF_2$, $CF_3CF_2CF_2CF_2CF_3$ and cyclo-$C_4F_8$; and fluorohalohydrocarbons such as $CHCl_2CCl_2F$, $CHClFCCl_3$, $CHCl_2CClF_2$, $CHClFCCl_2F$, $CHCl_2CF_3$, $CHBrClCF_3$, $CHBr_2CF_3$, $CHClFCF_3$, $CHF_2CClF_2$, $CHF_2CF_3$, $CH_2ClCCl_2F$, $CH_2FCCl_3$, $CF_3CH_2Cl$, $CHF_2CHF_2$, $CF_3CH_2F$, $CHFCH_2Cl$, $CCl_2FCH_3$, $CClF_2CH_3$, $CF_3CH_3$, $CHF_2CH_3$, $CH_2FCH_3$, $CF_3CF_2CHCl_2$, $CHClFCF_2CClF_2$, $CHClFCF_2CF_3$, $CHF_2CF_2CClF_2$, $CHF_2CF_2CClF_2$, $CF_3CF_2CHF_2$, $CHF_2CF_2CHClF$, $CF_3CCl_2CH_3$, $CHF_2CClFCF_3$, $CCl_2FCF_2CH_3$, $CH_3CF_2CHCl_2$, $CH_3CH_2CCl_2F$, $CF_3CF_2CH_3$, $CH_3CH_2CHClF$, $CH_3CHFCH_3$, $CH_3CH_2CH_2F$, $(CF_3)_2CHCCl_3$, $(CF_3)_2CHCF_3$ and $CF_3CF_2CF_2CH_2Cl$.

The invention process is capable of removing a wide variety of carbon-carbon unsaturated compounds when present in the saturated carrier compound, notably $C_2$ to $C_6$ olefins and optionally bearing halogen substituents, generally fluorine, chlorine and/or bromine and boiling over a wide range. The invention process is particularly effective for the removal of the $C_2$ olefins, which are commonly present in the fluorohalocarbons and fluorohalohydrocarbons described above.

Representative unsaturated impurities that can be removed from the saturated fluorohalocarbons and fluorohalohydrocarbons include hydrocarbon and halocarbon olefins, including the cis and trans isomers when they exist, such as: $CH_2=CH_2$, $CH_2=CHCl$, $CHCl=CHCl$, $CH_2=CCl_2$, $CHCl=CCl_2$, $CCl_2=CCl_2$, $CF_2=CH_2$, $CF_2=CHCl$, $CClF=CF_2$, $CClF=CCl_2$, $CHCl=CClF$, $CHF=CCl_2$, $CHF=CHCl$, $CH_2=CClF$, $CHF=CHF$, $CF_2=CCl_2$, $CF_2=CClF$, $CF_2=CBrCl$, $CF_2=CF_2$, $CF_2=CHF$, $CHF=CClF$, $CH_3CF=CH_2$, $CF_3CCl=CHCl$, $CF_3CCl=CF_2$, $CF_3CCl=CCl_2$, $CF_3CF=CF_2$; $CF_3CCl=CFCF_3$, $CF_3CH=CHCF_3$, $CF_3CCl=CHCF_3$, $CF_3CCl=CClCF_3$, $CF_3CF=CFCF_3$, $(CF_3)_2C=CF_2$, $CClF_2CF_2CF=CF_2$, $CF_3CH=CBrCF_3$, $CF_3CCl=CBrCF_3$, $CF_3CBr=CBrCF_3$.

Since the majority of the unsaturated compounds in the saturated fluorohalocarbons and halohydrocarbons is usually removable at reasonable cost by standard physical methods such as fractional distillation, the quantity of the unsaturated impurities remaining to be treated by the method of this invention will generally be less than about 1% by weight, and more usually will lie in the range of about 0.5% down to about 0.001% by weight of the saturated compound, or about 5000 ppm down to about 10 ppm. The invention process has been found effective in lowering the unsaturate content to below 10 ppm and, in most cases, to below the gas chromatographic detection limit.

The invention process is especially applicable to the purification of saturated fluorohalocarbons and fluorohalohydrocarbon products obtained by reaction of HF with a chlorine- or bromine-containing precursor of the fluorine-containing compound or compounds. Included, for example, are one or more of $CH_3CCl_2F$, $CH_3CClF_2$, and $CH_3CF_3$, contaminated with vinylidene chloride ($CH_2=CCl_2$), obtained by hydrofluorination of vinylidene chloride or methyl chloroform in the presence or absence of catalyst; $CF_3CH_2Cl$ and/or $CF_3CH_2F$ obtained by catalytic reaction of HF with $CX_3CH_2Cl$ or $CX_2=CHCl$, where X=Cl or F, and containing 1,1-difluoro-2-chloroethylene ($CF_2=CHCl$) as impurity; $CF_3CHCl_2$, $CF_3CHClF$ and $CF_3CHF_2$, obtained by catalytic reaction of HF with $CCl_2=CCl_2$ or $CCl_3CHCl_2$ and contaminated with one or more olefins such as $CF_2=CClF$, cis and trans $CF_3CCl=CFCF_3$ and $CF_3CCl=CHCF_3$; and $CF_3CHBrCl$, produced, for example, by chlorination of $CF_3CH_2Br$, bromination of $CF_3CH_2Cl$ or aluminum halide-catalyzed rearrangement of $CF_2BrCHClF$ and contaminated with one or more of $CF_3CX=CYCF_3$ or $CF_2=CClZ$, where X is F, Cl or Br, Y is Cl or Br and Z is H, Cl, Br or F. All these reactions and the conditions employed are described in the prior art.

The impure saturated compound to be treated should be in a substantially dry fluid, i.e., gaseous or liquid, state containing no more than about 1% by weight (10,000 ppm) water at the processing temperature. Compounds that are solid at the temperature required for the removal of their unsaturated impurities can be employed as solute in a dry liquid carrier which can be another saturated halocarbon or other saturated solvent inert to the metal oxide components of the reaction mixture. In such embodiments involving liquid compositions of saturated compounds to be purified, the liquid composition, as neat liquid or a solution of solid in a suitable solvent, may be mixed with the particulate metal oxide reactant and maintained under agitation at the desired temperature until the desired low level of unsaturated impurity is achieved. Alternatively, the liquid composition to be treated can be passed through a fixed bed of the metal oxide in a flow-through reactor. The treatment can be repeated with fresh metal oxide if necessary to achieve the desired result. The saturated product is then recovered substantially unsaturate-free by distillation or other physical method known to the art.

Inasmuch as the primary function of the metal oxide reactant is to remove unsaturated impurities from the halocarbons, the halocarbon being treated should, in addition to being substantially water-free, also be substantially free of substances that may interfere with the primary function of the metal oxide, particularly of hopcalite-type mixed metal oxides described further herein. Typical potentially interfering substances are carbon monoxide, hydrogen gas, hydrogen halides, hydrogen sulfide, sulfur dioxide and volatile organic hydroxylic compounds.

The metal oxide composition consists essentially of substantially dry amorphous solid cupric oxide, silver oxide, cobaltic oxide, manganese dioxide or a mixture of two or more of these metal oxides. It can be used alone in a particular form, e.g., in powdered or granular form, or carried dispersed on a substantially inert support such as carbon, alumina or titania.

The metal oxide composition may contain lower valent cationic members of the metallic elements. Thus, the cupric oxide, CuO, may contain cuprous oxide, $CuO_2$. Similarly the cobaltic oxide, $Co_2O_3$, may contain cobaltous oxide, CoO, and may be present as the equimolar cobaltous-cobaltic oxide, $CoO.Co_2O_3$ or $Co_3O_4$. Silver oxide is normally present substantially completely in the univalent state.

As is well-known, manganese dioxide, $MnO_2$, tends to be non-stoichiometric, its tetravalent Mn content and associated oxygen content varying with the method of preparation and subsequent handling of the oxide composition. As used herein, the term manganese dioxide is meant to include manganese oxide compositions wherein at least about one-half the Mn content is tetravalent and the average valence is at least about three. In other words, the manganese dioxide composition, $MnO_X$, where the O/Mn ratio X is normally and preferably 2, may contain a lower than stoichiometric oxygen content such that the O/Mn ratio is as low as 1.5, but preferably is at least 1.75. Thus, manganese dioxide compositions can be employed corresponding to a manganite type empirical formula, such as $MnO_2.MnO$ or $Mn_2O_3$. Further, since manganese dioxide is often and conveniently prepared by reduction of a permanganate, the oxide composition may contain minor proportions of manganese in the higher-valent manganate and permanaganate oxidation states.

Preferred metal oxide compositions are amorphous or homogeneous intimate mixtures, including hopcalite type mixtures, of two or more of the above metal oxides, in particular such mixtures consisting essentially of manganese dioxide and one or more of the other metal oxides, more preferably manganese dioxide and cupric oxide, with or without cobaltic and/or silver oxide also incorporated therein. The mixed oxides containing manganese dioxide are more effective for the purposes of this invention than either manganese dioxide or the other metal oxide or oxides used alone.

The manganese dioxide content of the mixed metal oxide composition can range from about 5 to 95% by weight of the metal oxides, preferably from about 45 to 90% by weight. Considered on a molar basis, the manganese dioxide content will preferably amount to at least 1 mole, taken as $MnO_2$, per mole of the other metal oxide or oxides combined, with each when present taken as CuO, $Ag_2O$ and $Co_2O_3$. The manganese dioxide is preferably in excess, in amounts corresponding to from about 1.3 to about 10 moles per mole of the other metal oxide or oxides, more preferably from about 1.5 to about 6 moles per mole.

The metal oxides may be prepared by any of the methods known to the art. They are best prepared by precipitation including co-precipitation from aqueous solution. This method yields finely divided, high surface area precipitates of the metals as hydroxides or hydrous oxides, which, after filtering and washing, convert to substantially dry amorphous solid oxides having high surface area and low bulk density on drying. They may also be granulated.

The copper, silver and cobalt oxides are conveniently precipitated by treating a soluble salt of the metal or metals, such as the sulfate or nitrate, with an alkali metal hydroxide. The precipitates are washed with water to remove soluble salts, including any excess alkali, dried at temperatures up to about 250° C., generally in a stream of air or other gaseous agent for entraining water, and granulated.

Alternatively, amorphous copper oxide can be prepared by first precipitating cupric carbonate, by treating aqueous copper sulfate with sodium carbonate, filtering, washing and pressing to partially dry the precipitate and heating at 180° to 250° C. to both dry and convert the carbonate to the oxide with liberation of carbon dioxide. Amorphous manganese dioxide having a high oxygen content, i.e., $MnO_X$ where X is at least 1.5, more usually at least 1.75, can be prepared by reaction of $MnSO_4$ in aqueous sulfuric acid with an alkali metal permanganate. It can also be prepared by reduction of a permanganate composition with methanol, oxalic acid or other readily oxidized organic hydroxylic compound, as is well-known in the art.

The oxidation state of copper in the cupric oxide, of cobalt in cobaltic oxide and of manganese in the manganese dioxide preparation can be determined, if desired or necessary, by standard analytical, usually redox methods.

The precipitation method is especially suitable for the preparation of amorphous, intimate mixtures of the metal oxides. Hydrous precipitates can be separately prepared as above, then well-blended while still in the form of hydroxides and/or hydrous oxides before drying. Or, co-precipitates of the individual metal hydroxides and/or hydrous oxides can first be prepared as described above and the co-precipitates treated as described above for the individual metal oxides. For example, an intimate mixture of cupric oxide and manganese dioxide can be prepared by adding an aqueous solution containing alkali metal hydroxide and alkali metal permanganate to an aqueous solution containing cupric sulfate and manganous sulfate under agitation. The co-precipitate is collected, washed well to remove soluble salts and alkali, dried and granulated in the usual manner. Alternatively, cupric oxide can be precipitated on a preformed still-wet precipitate of manganese dioxide, the mixture intimately blended, then washed and dried as before.

Drying of the amorphous metal oxide compositions can be carried out at temperatures up to about 300° C., preferably not above about 250° C. to minimize possible loss of surface area, porosity, amorphous character and activity for the intended purpose.

Metal oxide compositions may, after drying, still retain bound water, perhaps as hydrates of the metal oxides, in amounts corresponding to as much as about 5% by weight of the composition, but are regarded as substantially dry for the purposes of the invention. Preferably the compositions are dried to less than 3% by weight water, more preferable to less than 1% by weight, the lower the water content the more active the metal oxide composition for unsaturate removal. It will be appreciated that drying of the metal oxide composition can take place through entrainment under the conditions of the unsaturate removal process, wherein the gaseous substrate to be treated is passed through a bed of the metal oxide composition so that, depending on the temperature employed, its unsaturates removal performance may improve with time. It will also be appreciated by those skilled in the art that the mixed metal oxide compositions that remain after drying at elevated temperatures are not necessarily simple mixtures containing discrete molecules of one oxide, such as CuO, and of another oxide such as $MnO_2$. For example, cupric oxide and manganese dioxide are known to form amorphous compositions wherein the individual oxides are no longer detectable as such; rather, they are regarded as complex copper manganites, such as $CuMn_2O_4$, which may be associated with additional molecular amounts of $MnO_2$ depending upon the relative proportions of copper and manganese used in the preparation of the mixed oxides. Silver oxide and cobaltic oxide behave similarly, forming complex oxides in their interactions with manganese dioxide. For the purposes of this invention however, the mixed oxides are conveniently described in terms of the individual oxides employed in their preparation.

Typical and satisfactory methods for the preparation of amorphous cupric, silver, cobaltic and manganese oxide compositions, including suitable amorphous hopcalite type intimate mixtures thereof produced by precipitation methods as outlined above are described in the Frazer and Scalione U.S. Pat. No. 1,345,323 above as well as in the following publications:
Lamb et al, J. Ind. Eng. Chem. 12(3)213 (1920);
Merrill et al, J. Am. Chem. Soc. 43 1982 (1921);
Almquist et al, J. Am. Chem. Soc. 45 2305 (1923);
Shigamatsu Seis, Jap. Patent 76-020477 (1976);
Tokarzewski and Lipinski, Polish Patent 99944 (1978).

Representative amorphous intimate mixtures consisting essentially of cupric oxide and manganese dioxide contain 13 to 48% by weight CuO and 87 to 52% by weight of $MnO_2$, preferably 13 to 33% by weight CuO and 87 to 67% by weight $MnO_2$, based on the total weight of the metal oxides. Representative amorphous intimate mixtures consisting essentially of silver oxide and manganese dioxide contain 35 to 73% by weight $Ag_2O$ and 65 to 27% by weight $MnO_2$. A typical amorphous, intimate mixture consisting essentially of cobaltic oxide and manganese dioxide contains about 39% by weight $Co_2O_3$ and 61% by weight $MnO_2$.

A representative amorphous, intimate mixture based on manganese dioxide in association with copper, silver and cobalt oxides contains about 5% $Ag_2O$, 15% $Co_2O_3$, 30% CuO and 50% $MnO_2$, all by weight of the metal oxide composition.

Cupric oxide-manganese dioxide mixed oxide compositions are available commercially as "hopcalite" catalysts and are suitable for use in the invention method without further processing. The commercial materials are described as amorphous, homogeneous mixtures or co-precipitates of the two oxides. The commercial compositions are understood to contain 14 to 33% by weight cupric oxide and 86 to 67% by weight manganese dioxide, and may contain up to about 5% by weight of bound water based on the total weight of the composition. These compositions are considered substantially dry for the purposes of this invention: compositions containing less than 3% by weight water are preferred. For best results, heating and purging with an inert gas such as nitrogen prior to use is usually advisable to bring the water content down to desired levels.

The process of the present invention is carried out at an effective temperature. By effective temperature is meant a temperature below that which will cause significant decomposition of the saturated fluorohalocarbons and fluorohalohydrocarbons to occur. This temperature can generally range up to about 300° C., preferably in the range of about 20° to about 180° C., more preferably in the range of about 50° to 150° C., and most preferably in the range of about 90° to 130° C., with the temperature required depending on the product stream to be treated and the result desired.

Pressure at which the purification is carried out does not appear critical. The vapor-phase embodiment is conveniently carried out at atmospheric pressure, although sub- and super-atmospheric pressures may also be used. The liquid-phase embodiment is carried out at pressures sufficient to maintain the saturated material to be treated in the liquid state, which pressure will vary depending on the operating temperature and the vapor pressure of the material being treated.

In the vapor-phase process, which is preferred for reasons of economy, the flow rate of the impure fluorinated product can vary widely, for example, from 5 to 20 pounds per hour of the impure material per cubic foot of metal oxide composition employed. The flow of impure material is continued until the impurity content of the exit stream again becomes detectable and approaches its defined maximum permissible concentration limit. At that point the flow of the impure material through the metal oxide bed is terminated or directed through one or more additional beds of fresh metal oxide composition maintained in series or in parallel with the first bed.

As noted earlier, the metal oxide compositions are effective in the absence of air or other source of molecular oxygen although such source may be employed if desired.

EXAMPLES

1.) To a 1" O.D. stainless steel tube 13" long was added 117.5 gms of a commercially available hopcalite consisting essentially of an amorphous co-precipitate of cupric oxide (14.8 wt. %) and manganese dioxide (85.2 wt. %) in the form of 6–14 mesh (U.S. sieve size) granules having a bulk density of about 3.7 gms/cc and a moisture content of less than about 3.0 wt. %. The tube was then connected to a source of $CF_3$—$CH_2F$ containing 850 ppm 1,1-difluoro-2-chloroethylene ($CF_2$=CHCl) which was admitted to the tube at a rate of 65–70 ml/minute. The exit stream composition was monitored by gas chromatography and showed no $CF_2$=CHCl present until 1669 minutes (27.8 hrs) had elapsed when 3.3 ppm of $CF_2$=CHCl was observed in the exit stream. Taking this as the "breakthough" point, the bed capacity at 25° C. is calculated to be 0.0050 gm of $CF_2$=CHCl removed per 1 gm of this hopcalite. There was no sign that $CF_3$—$CH_2F$ was lost due to oxidation, and neither hydrogen halides nor water was observed in the exit stream. Carbon dioxide was observed in the exit stream, however, and the amount corresponded approximately to the amount of $CF_2$=CHCl fed.

2.) The procedure in (1) was followed except the reactor tube was maintained at 50° C. in a tube furnace. After 2880 minutes (48 hrs), 11.2 ppm of $CF_2$=CHCl was observed in the exit stream and this was taken as the "breakthrough" point. Bed capacity was calculated to be 0.0092 gm of $CF_2$=CHCl per gm of this hopcalite.

3.) The procedure in (1) was followed except the reactor tube was maintained at 130° C. and feed rate was varied from 70 to 700 ml/minute. After 12240 minutes (204 hrs), 10.0 ppm of $CF_2$=CHCl was observed in the exit stream, and this was taken as the "breakthrough" point. Bed capacity is calculated to be 0.0299 gm of $CF_2=CHCl$ per gm of this hopcalite.

4.) The procedure in (2) was followed except the feed rate was maintained at 700 ml/minute. After 95 minutes, 11.1 ppm of $CF_2=CHCl$ was observed in the exit stream, and this was taken as the "breakthrough" point. Bed capacity is calculated to be 0.0092 gm of $CF_2=CHCl$ per gm of this hopcalite, identical with the Example 2 run at 1/10th the feed rate.

5.) To a 1" O.D. stainless steel tube 13" long was added 115.3 gms of the hopcalite of Example 1. The tube was than placed in a tube furnace at a temperature of 100° C., and a mixture of 1-chloro-1,1-difluoroethane, $CH_3-CClF_2$, and 1,1-dichloro-1-fluoroethane, $CH_3CCl_2F$, containing ca. 900 ppm of vinylidene chloride ($CH_2=CCl_2$) vapor was admitted to the tube at a constant rate of 65–70 ml/minute. The exit stream composition was monitored by gas chromatography for 2 hours and showed no vinylidene chloride present. There was no sign that $CH_3-CCl_2F$ or $CH_3-CClF_2$ was oxidized or in any other way affected during the run.

6.) To a 1" O.D. stainless steel tube 13" long was added 119.4 gms of the hopcalite previously described in Example 1. The tube was then placed in a tube furnace at a temperature of 100° C., and $CF_3-CH_2F$ to which had been added 500 ppm of each of the following unsaturates (to illustrate the versatility of the process) was admitted to the tube at a constant rate of 70 ml/minute for 2.5 hours.

| Compound Designation* | Structure |
|---|---|
| CFC-1112 | (CClF=CClF) |
| CFC-1112a | ($CF_2=CCl_2$) |
| CFC-1113 | ($CF_2=CClF$) |
| FC-1114 | ($CF_2=CF_2$) |
| HCFC-1122 | ($CF_2=CHCl$) |
| HFC-1123 | ($CF_2=CHF$) |
| HCFC-1131a | ($CH_2=CClF$) |
| HFC-1132a | ($CF_2=CH_2$) |
| HCC-1140 | ($CH_2=CHCl$) |
| HC-1150 | ($CH_2=CH_2$) |

*Compound Designation as described in by J. M. Hamilton in "The Organic Fluorochemicals Industry", Advances in Fluorine Chemistry, Vol 3, Appendix A.

The exit stream composition was monitored by gas chromatography and showed no unsaturates present.

7.) To a 1" O.D. stainless steel tube 13" long was added 111.4 gms of the previously described hopcalite of Example 1. The tube was then placed in a tube furnace, heated to 130° C., and 2-chloro-1,1,1,2-tetrafluoroethane ($CF_3CHClF$) containing ca. 7000 ppm of chlorotrifluoroethylene ($CF_2=CFCl$) was admitted to the tube at a rate of 200 ml/minute. The exit stream composition was monitored by gas chromatography. After 3.8 hr, 10.0 ppm of $CF_2=CFCl$ was observed in the exit stream, and this was taken as the "breakthrough" point. Bed capacity is calculated to be 0.0170 gm of $CF_2=CFCl$ per gm of this hopcalite.

8.) To a 1" O.D. stainless steel tube 13" long was added 113.4 gms of the previously described hopcalite of Example 1. The tube was then placed in a tube furnace at a temperature of 130° C., and 2,2-dichloro-1,1,1-trifluoroethane ($CF_3-CCl_2H$) to which had been added each of the following unsaturates, in the specified concentration, was admitted to the tube at a constant rate of 100 ml of vapor/minute.

| Compound Designation | Structure | ppm (in) | ppm (out) |
|---|---|---|---|
| HFC-1261yf | ($CH_3-CF=CH_2$) | 481 | 0 |
| HCFC-1223xd | ($CF_3-CCl=CClH$) | 717 | 21 |
| CFC-1215xc | ($CF_3-CCl=CF_2$) | 930 | 0 |
| CFC-1214xb | ($CF_3-CCl=CFCl$) | 757 | 76 |
| CFC-1213xa | ($CF_3-CCl=CCl_2$) | 791 | 0 |
| FC-1318my | ($CF_3-CF=CF-CF_3$) | 1000 | 590 |
| CFC-1317mx | ($CF_3-CCl=CF-CF_3$) | 454 (trans) | 132 |
| CFC-1317mx | ($CF_3-CCl=CF-CF_3$) | 303 (cis) | 55 |
| HFC-1336 | ($CF_3-CH=CH-CF_3$) | 262 | 155 |
| HCFC-1326mxz | ($CF_3-CCl=CH-CF_3$) | 401 | 209 |
| HCFC-1326 | (ISOMER) | 42 | 5 |
| CFC-1316mxx | ($CF_3-CCl=CCl-CF_3$) | 397 (trans) | 24 |
| CFC-1316mxx | ($CF_3-CCl=CCl-CF_3$) | 398 (cis) | 20 |

The exit stream composition was monitored by gas chromatography and showed significant reduction, if not complete removal, of all unsaturates after 30 minutes of operation. The results indicate that additional treatment of the exit stream with fresh beds of hopcalite would further lower the unsaturate content eventually to below 10 ppm. The results also show the difference in efficiency of this hopcalite for removing unsaturates of different structures.

9.) To a 1" O.D. stainless steel tube 13" long was added 15.8 gms of dry CuO. The tube was then placed in a tube furnace at a temperature of 100° C., and $CF_3-CH_2F$ containing 500 ppm of each of the following unsaturates was admitted to the tube at a constant rate of 20 ml/minute for 5.0 hours.

| Compound Designation | Structure |
|---|---|
| CFC-1112 | (CClF=CClF) |
| CFC-1112a | (CF2=CCl2) |
| CFC-1113 | (CF2=CClF) |
| FC-1114 | (CF2=CF2) |
| HCFC-1122 | (CF2=CHCl) |
| HFC-1123 | (CF2=CHF) |
| HCFC-1131a | (CH2=CClF) |
| HFC-1132a | (CF2=CH2) |
| HCC-1140 | (CH2=CHCl) |
| HC-1150 | (CH2=CH2) |

The exit stream composition was monitored by gas chromatography. Under these conditions, FC-1114, HCFC-1122, and CFC-1112a were removed completely, while the other unsaturates were unaffected.

10.) To a 1" O.D. stainless steel tube 13" long was added 32.7 gms of 50% $MnO_2$ on activated carbon. The tube was then placed in a tube furnace at a temperature of 100° C., and $CF_3-CH_2F$ containing 500 ppm of each of the following unsaturates was admitted to the tube at a constant rate of 20 ml/minute for 3.5 hours.

| Compound Designation | Structure |
|---|---|
| CFC-112 | (CClF=CClF) |
| CFC-1112a | (CF2=CCl2) |
| CFC-1113 | (CF2=CClF) |
| FC-1114 | (CF2=CF2) |
| HCFC-1122 | (CF2=CHCl) |
| HFC-1123 | (CF2=CHF) |
| HCFC-1131a | (CH2=CClF) |
| HFC-1132a | (CF2=CH2) |

| Compound Designation | Structure |
|---|---|
| HCC-1140 | ($CH_2$=CHCl) |
| HC-1150 | ($CH_2$=$CH_2$) |

The exit stream composition was monitored by gas chromatography. Under these conditions, HCFC-1131a, HCC-1140, CFC-1113, HCFC-1122, CFC-1112a, and CFC-1112 were removed completely, while the other unsaturates were unaffected.

11.) To a 14" length of ¼" O.D. Inconel tubing was added 5.1 gms of cobalt (II,III) oxide, $Co_3O_4$. The tube was then placed in a tube furnace at 100° C., and $CF_3$—$CH_2F$ containing 559 ppm of 1,1-difluoro-2-chloroethylene ($CF_2$=CHCl), was admitted to the tube at a rate of 13.5 ml/minute. The exit stream composition was monitored by gas chromatography for 5.0 hrs; the $CF_2$=CHCl concentration was reduced by ca. 90% during this period of time.

I claim:

1. A process for reducing the content of unsaturated impurities in a saturated fluorohalocarbon, which process comprises contacting said fluorohalocarbon having 2-6 carbon atoms wherein halo represents fluoro, chloro and bromo substituents containing one or more unsaturated impurities in a substantially dry fluid state with a substantially dry amorphous solid metal oxide composition consisting essentially of cupric oxide, silver oxide, cobaltic oxide, manganese dioxide or a mixture of any two or more of said cupric oxide, silver oxide, cobaltic oxide, and manganese dioxide, at a temperature up to about 300° C. and below that which will cause significant decomposition of the saturated fluorohalocarbon to occur, and recovering said saturated fluorohalocarbon having a reduced content of said one or more unsaturated impurities and without substantial yield loss of the saturated fluorohalocarbon.

2. The process of claim 1 wherein said fluorohalocarbon is gaseous at said temperature.

3. The process of claim 1 wherein the fluorohalocarbon has a normal boiling point in the range between about −40° C. to about 120° C.

4. The process of claim 1 wherein the metal oxide composition is an intimate mixture of any two or more of cupric oxide, silver oxide, cobaltic oxide and manganese dioxide.

5. The process of claim 4 wherein manganese dioxide is present in the metal oxide composition.

6. The process of claim 5 wherein the metal oxide composition is a hopcalite having a manganese dioxide content of from about 5% to about 95% by weight of the metal oxide composition.

7. The process of claim 6 wherein cupric oxide is present in the metal oxide composition.

8. The process of claim 7 wherein the metal oxide composition consists essentially of manganese dioxide and cupric oxide.

9. The process of claim 4 wherein the metal oxide composition has from about 45% to about 90% by weight of manganese calculated as the dioxide and from about 55% to about 10% by weight of copper calculated as cupric oxide based on the total weight of the metal oxide composition.

10. The process of claim 8 wherein the metal oxide composition has about 13% to 48% cupric oxide and about 87% to 52% manganese dioxide based on the total weight of the metal oxide composition.

11. The process of claim 10 wherein the metal oxide composition has about 13% to 33% cupric oxide and about 87% to 67% manganese dioxide based on the total weight of the metal oxide composition.

12. The process of claim 8 wherein the metal oxide composition also includes silver oxide and/or cobaltic oxide.

13. The process of claim 1 where (a) the metal oxide composition is an amorphous hopcalite having from about 10% to about 55% by weight of copper calculated as cupric oxide and from about 90% to about 45% by weight of manganese calculated as manganese dioxide; and (b) contact between the fluorohalocarbon and the metal oxide composition is maintained at from about 50° C. to 150° C. until the content of one or more of said unsaturated impurities in the saturated fluorohalocarbon has been reduced to below 10 ppm.

14. The process of claim 1 wherein the temperature is in the range of from about 50° C. to about 150° C.

15. The process of claim 14 wherein the temperature is in the range of from about 90° C. to about 130° C.

* * * * *